US012688666B2

(12) United States Patent (10) Patent No.: US 12,688,666 B2
Geoly et al. (45) Date of Patent: Jul. 21, 2026

(54) SYSTEMS AND METHODS FOR ENTROPY-BASED TREATMENT

(71) Applicant: The Board of Trustees of the Leland Stanford Junior University, Stanford, CA (US)

(72) Inventors: Andrew Geoly, Stanford, CA (US); Nolan R. Williams, Half Moon Bay, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 631 days.

(21) Appl. No.: 17/933,440

(22) Filed: Sep. 19, 2022

(65) Prior Publication Data

US 2023/0091727 A1 Mar. 23, 2023

Related U.S. Application Data

(60) Provisional application No. 63/245,741, filed on Sep. 17, 2021.

(51) Int. Cl.
*G16H 30/40* (2018.01)
*G06V 10/25* (2022.01)
(Continued)

(52) U.S. Cl.
CPC ............ *G06V 10/25* (2022.01); *G06V 10/761* (2022.01); *G16H 20/10* (2018.01); *G16H 20/30* (2018.01)

(58) Field of Classification Search
CPC ...... G06V 10/25; G06V 10/761; G16H 20/10; G16H 20/30; G16H 50/30; G16H 50/50; G16H 30/40
See application file for complete search history.

(56) References Cited

U.S. PATENT DOCUMENTS

| | | |
|---|---|---|
| 7,706,871 B2 | 4/2010 | Devlin |
| 10,595,735 B2 | 3/2020 | Williams et al. |

OTHER PUBLICATIONS

Wohlschläger, Afra, et al. "Spectral dynamics of resting state fMRI within the ventral tegmental area and dorsal raphe nuclei in medication-free major depressive disorder in young adults." Frontiers in psychiatry 9 (Year: 2018).*

(Continued)

*Primary Examiner* — Stephen R Koziol
*Assistant Examiner* — Dylan J Sherrillo
(74) *Attorney, Agent, or Firm* — KPPB LLP

(57) ABSTRACT

Systems and methods for entropy-based treatment in accordance with embodiments of the invention are illustrated. One embodiment includes a method for treating a neurological condition, including obtaining a functional magnetic resonance imaging (fMRI) scan of a patient's brain, identifying a plurality of regions of interest (ROIs) in the fMRI scan, calculating entropy metrics for each ROI in the plurality of ROIs, selecting a treatment from a plurality of treatments for the neurological condition based on the entropy metrics, and provide the selected treatment to the patient. In a further embodiment, calculating entropy metrics includes generating multiscale entropy curves for each ROI, calculating the area under each entropy curve, assigning each ROI as positive or negative sign based on the entropy curve of each ROI, generating a similarity index for each ROI, and signing the similarity index for each ROI using the assigned sign of each ROI.

20 Claims, 4 Drawing Sheets

(51) Int. Cl.
  *G06V 10/74* (2022.01)
  *G16H 20/10* (2018.01)
  *G16H 20/30* (2018.01)

(56) References Cited

OTHER PUBLICATIONS

Baeken, Chris, et al. "Subgenual anterior cingulate-medial orbitofrontal functional connectivity in medication-resistant major depression: a neurobiological marker for accelerated intermittent theta burst stimulation treatment?." Biological Psychiatry: Cognitive Neuroscience and Neuroimaging 2.7 (Year: 2017).*

Xia, Kelin, Zhiming Li, and Lin Mu. "Multiscale persistent functions for biomolecular structure characterization." Bulletin of mathematical biology 80.1 (2018): 1-31. (Year: 2018).*

Shalbaf, Reza, et al. "Non-linear entropy analysis in EEG to predict treatment response to repetitive transcranial magnetic stimulation in depression." Frontiers in Pharmacology 9 (2018): 1188. (Year: 2018).*

Fu et al., "Integrating Optimized Multiscale Entropy Model with Machine Learning for the Localization of Epileptogenic Hemisphere in Temporal Lobe Epilepsy Using Resting-State fMRI", Journal of Healthcare Engineering, Oct. 27, 2021, vol. 2021, Article ID 1834123, 10 pages, https://doi.org/10.1155/2021/1834123.

Shalbaf et al., "Non-linear Entropy Analysis in EEG to Predict Treatment Response to Repetitive Transcranial Magnetic Stimulation in Depression", frontiers in Pharmacology, Oct. 30, 2018, vol. 9, Article 1188, 11 pgs., doi: 10.3389/fphar.2018.01188.

Costa et al., "Multiscale Entropy Analysis of Complex Heart Rate Dynamics: Discrimination of Age and Heart Failure Effects", Computers in Cardiology, vol. 30, 2003, pp. 705-708, doi: 10.1109/CIC.2003.1291253.

Farzan et al., "Enhancing the Temporal Complexity of Distributed Brain Networks with Patterned Cerebellar Stimulation", Scientific Reports, vol. 6, Article 23599, Mar. 24, 2016, 9 pgs., doi: 10.1038/srep23599.

Leistedt et al., "Decreased neuroautonomic complexity in men during an acute major depressive episode: analysis of heart rate dynamics", Translational Psychiatry, vol. 1, Article e27, Jul. 2011, 7 pgs., doi: 10.1038/tp.2011.23.

McDonough et al., "Network complexity as a measure of information processing across resting-state networks: evidence from the Human Connectome Project", Frontiers in Human Neuroscience, vol. 8, Article 409, Jun. 10, 2014, 15 pgs., doi: 10.3389/fnhum.2014.00409.

Niu et al., "Dynamic Complexity of Spontaneous BOLD Activity in Alzheimer's Disease and Mild Cognitive Impairment Using Multiscale Entropy Analysis", Frontiers in Neuroscience, Original Research, vol. 12, Article 677, Oct. 1, 2018, 13 pgs., doi: 10.3389/fnins.2018.00677.

Omidvarnia et al., "Temporal complexity of fMRI is reproducible and correlates with higher order cognition", NeuroImage, vol. 230, Article 117760, Apr. 15, 2021, 12 pgs., doi: 10.1016/j.neuroimage.2021.117760.

Sokunbi et al., "Resting state fMRI entropy probes complexity of brain activity in adults with ADHD", Psychiatry Research: Neuroimaging, vol. 214, No. 3, Dec. 30, 2013, pp. 341-348, doi: 10.1016/j.pscychresns.2013.10.001.

Takahashi et al., "Antipsychotics reverse abnormal EEG complexity in drug-naive schizophrenia: A multiscale entropy analysis", NeuroImage, vol. 51, No. 1, May 15, 2010, pp. 173-182, doi: 10.1016/j.neuroimage.2010.02.009.

Wang et al., "Neurophysiological Basis of Multi-Scale Entropy of Brain Complexity and Its Relationship With Functional Connectivity", Frontiers in Neuroscience, Hypothesis and Theory, vol. 12, Article 352, May 29, 2018, 14 pgs., doi: 10.3389/fnins.2018.00352.

* cited by examiner

300

Begin

310 — Obtain brain imaging data describing patient's brain

320 — Identify regions of interest (ROI)

330 — Generate multiscale entropy curves for each ROI

340 — Calculate entropy metrics

350 — Provide treatment determination

360 — Provide determined treatment to patient

End

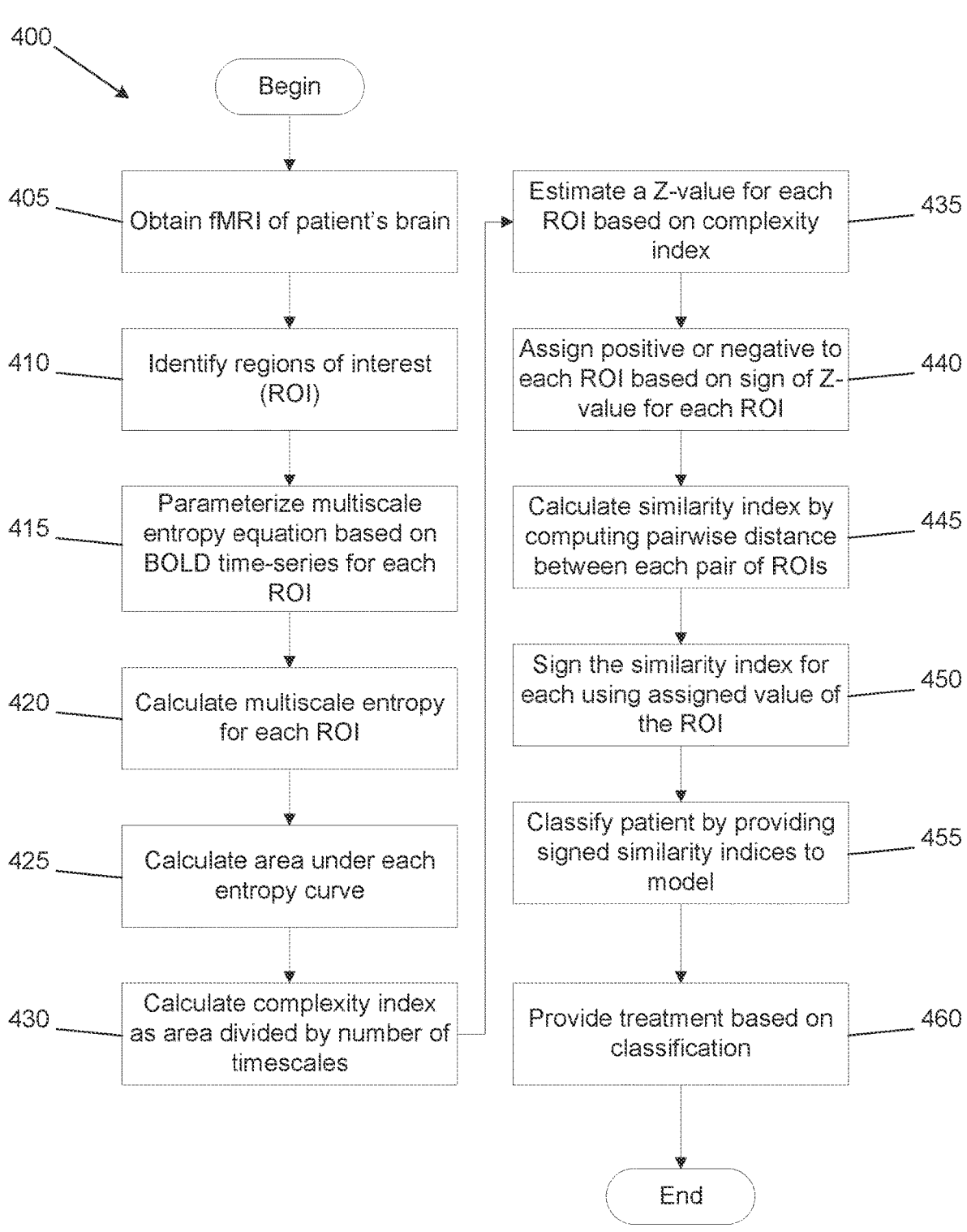

400

Begin

405 — Obtain fMRI of patient's brain

410 — Identify regions of interest (ROI)

415 — Parameterize multiscale entropy equation based on BOLD time-series for each ROI 420 — Calculate multiscale entropy for each ROI 425 — Calculate area under each entropy curve 430 — Calculate complexity index as area divided by number of timescales 435 — Estimate a Z-value for each ROI based on complexity index 440 — Assign positive or negative to each ROI based on sign of Z-value for each ROI 445 — Calculate similarity index by computing pairwise distance between each pair of ROIs 450 — Sign the similarity index for each using assigned value of the ROI 455 — Classify patient by providing signed similarity indices to model 460 — Provide treatment based on classification End

*FIG. 4*

SYSTEMS AND METHODS FOR ENTROPY-BASED TREATMENT

CROSS-REFERENCE TO RELATED APPLICATIONS

The current application claims the benefit of and priority under 35 U.S.C. § 119(e) to U.S. Provisional Patent Application No. 63/245,741 entitled "Systems and Methods for Entropy-Based Treatment" filed Sep. 17, 2021. The disclosure of U.S. Provisional Patent Application No. 63/245,741 is hereby incorporated by reference in its entirety for all purposes.

FIELD OF THE INVENTION

This invention generally relates to using information entropy to generate identifying personalized treatment options for neurological conditions.

BACKGROUND

In information theory, as conceived and described by Claude Shannon in "A Mathematical Theory of Communication" in 1948, the entropy of a random variable is the average level of "information" inherent in the variable's possible outcomes.

The human brain is a highly complex organ made of many different structures which are interconnected. Different regions and subregions are functionally connected, and there are numerous known "networks" that exist within the brain that have various known and yet unknown functionalities.

SUMMARY OF THE INVENTION

Systems and methods for entropy-based treatment in accordance with embodiments of the invention are illustrated. One embodiment includes a method for treating a neurological condition, including obtaining a functional magnetic resonance imaging (fMRI) scan of a patient's brain, identifying a plurality of regions of interest (ROIs) in the fMRI scan, calculating entropy metrics for each ROI in the plurality of regions of interest, selecting a treatment from a plurality of treatments for the neurological condition based on the entropy metrics, and provide the selected treatment to the patient.

In another embodiment, wherein the neurological condition is major depressive disorder, and the plurality of treatments comprise accelerated theta burst stimulation (aTBS) and pharmacological treatment.

In a further embodiment, calculating entropy metrics includes generating multiscale entropy curves for each ROI, calculating the area under each entropy curve, assigning each ROI as positive or negative sign based on the entropy curve of each ROI, generating a similarity index for each ROI, and signing the similarity index for each ROI using the assigned sign of each ROI.

In still another embodiment, selecting a treatment further includes providing the signed similarity index to a machine learning model.

In a still further embodiment, the machine learning model is trained using a training data set including signed similarity indices annotated with treatment outcomes.

In yet another embodiment, the machine learning model is a Naïve-Bayes model.

In a yet further embodiment, generating multiscale entropy curves for each ROI includes parameterizing a multiscale entropy equation such that $\tau$ is set such that a number of samples per time-scale is greater than 50.

In another additional embodiment, assigning each ROI as positive or negative sign includes performing a Z-transform.

In a further additional embodiment, generating a similarity index includes calculating pairwise distance between each pair of ROIs based on the entropy curves.

In another embodiment again, pairwise distance is calculated using Manhattan distance.

In a further embodiment again, a system for treating a neurological condition includes a processor, and a memory, the memory containing a treatment prediction application that configures the processor to: obtain a functional magnetic resonance imaging (fMRI) scan of a patient's brain, identify a plurality of regions of interest (ROIs) in the fMRI scan, calculate entropy metrics for each ROI in the plurality of regions of interest, select a treatment from a plurality of treatments for the neurological condition based on the entropy metrics, and provide the selected treatment as a recommended treatment for the patient.

In still yet another embodiment, the neurological condition is major depressive disorder, and the plurality of treatments comprise accelerated theta burst stimulation (aTBS) and pharmacological treatment.

In a still yet further embodiment, to calculate entropy metrics, the treatment prediction application further directs the processor to: generate multiscale entropy curves for each ROI, calculate the area under each entropy curve, assign each ROI as positive or negative sign based on the entropy curve of each ROI, generate a similarity index for each ROI, and sign the similarity index for each ROI using the assigned sign of each ROI.

In still another additional embodiment, to select a treatment, the treatment prediction application further directs the processor to provide the signed similarity index to a machine learning model.

In a still further additional embodiment, the machine learning model is trained using a training data set including signed similarity indices annotated with treatment outcomes.

In still another embodiment again, the machine learning model is a Naïve-Bayes model.

In a still further embodiment again, to generate multiscale entropy curves for each ROI, the treatment prediction application further directs the processor to parameterize a multiscale entropy equation such that $\tau$ is set such that a number of samples per time-scale is greater than 50.

In yet another additional embodiment, to assign each ROI as positive or negative sign, the treatment prediction application further directs the processor to perform a Z-transform.

In a yet further additional embodiment, to generate a similarity index, the treatment prediction application further directs the processor to calculate pairwise distance between each pair of ROIs based on the entropy curves.

In yet another embodiment again, pairwise distance is calculated using Manhattan distance.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

FIG. 4 is a flow chart for another entropy-based treatment method in accordance with an embodiment of the invention.

DETAILED DESCRIPTION

Major depressive disorder is an unfortunately common condition which severe consequences. However, many different treatment protocols have been developed, from pharmacological options, to therapies, to neurostimulation such as (but not limited to) transcranial magnetic stimulation and electroconvulsive therapy. Selecting which treatment will be most effective for a particular patient is a difficult task. Each person is different with their own particular neurological idiosyncrasies. In order to aid in rapid delivery of effective treatment, systems and methods described herein can provide an entropy-based process for selecting the most suited treatment option for a given patient. In numerous embodiments, specific therapies can be noted as unlikely to provide sufficient relief or more likely to provide sufficient relief.

In various embodiments, entropy for different regions of interest in the brain are determined. In many embodiments, the regions of interest are brain structures (or portions thereof) that are known to be related to a particular neurological condition such as (but not limited to) major depressive disorder. The multiscale sample entropy (SampEn) can be used to calculate entropy from blood-oxygen-level-dependent (BOLD) signals for the different regions of interest. Complexity indices can be calculated and depending on the amount of complexity in the regions of interest, different treatment options can be implicated as having a higher likelihood of efficacy for the particular patient.

Figure 1:
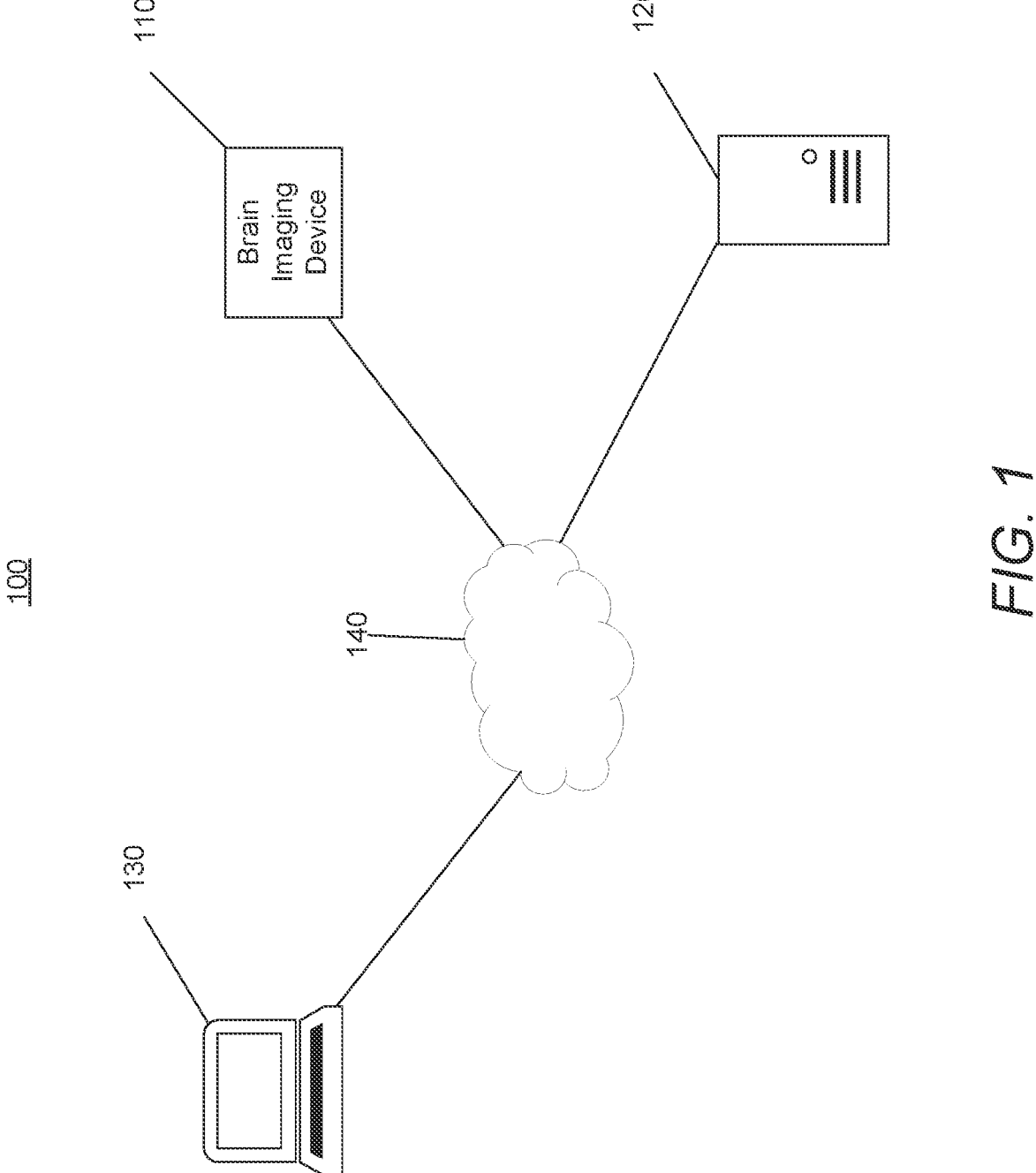
FIG. 1 is an entropy-based treatment system in accordance with an embodiment of the invention.

Turning now to FIG. 1, an entropy-based prescription system in accordance with an embodiment of the invention is illustrated. System 100 includes a brain imaging device 110. In many embodiments, the brain imaging device is a functional magnetic resonance imaging machine. System 100 further includes a controller 120 that provides computing capabilities for carrying out various entropy-based treatment processes. System further includes a display device 130 capable of providing human-comprehensible output to medical professionals. Individual devices in system 100 can communicate via network 140. In some embodiments, not all devices are connected via the network. In various embodiments, the network is the Internet. However, the network can be any type of network and/or combination of networks, either wired and/or wireless, as appropriate to the requirements of specific applications of embodiments of the invention.

Figure 2:
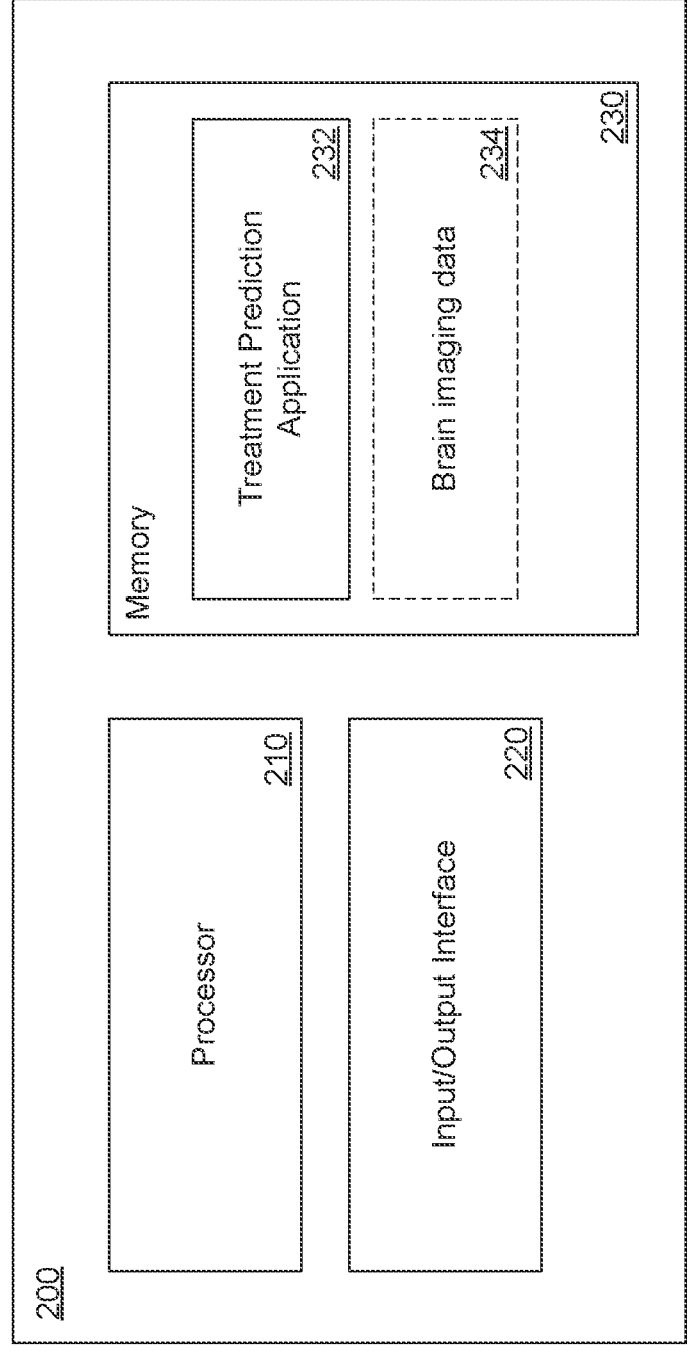
FIG. 2 is a block diagram for a controller in accordance with an embodiment of the invention.

Turning now to FIG. 2, a controller in accordance with an embodiment of the invention is illustrated. Controller 200 includes a processor 210. Processor 210 can be any logic circuitry capable of performing entropy-based treatment processes as appropriate to the requirements of specific applications of embodiments of the invention. For example, processor 210 can be implemented using a central processing unit (CPU), graphics processing unit (GPU), application-specific integrated circuit (ASIC), field-programmable gate array (FPGAs), and/or any other logic processing circuitry or combination thereof. Controller 200 further includes an input/output (I/O) interface 220. I/O interfaces can enable communication with other devices.

The controller 200 further includes a memory 230. The memory can be implemented using volatile memory, nonvolatile memory, or any combination thereof. The memory 230 contains a treatment prediction application 232 which can direct the processor to carry out entropy-based treatment processes. In various embodiments, the memory 230 further includes brain imaging data 234 for a particular patient. In numerous embodiments, the brain imaging data is functional magnetic resonance imaging (fMRI) data. While particular architectures are illustrated in FIGS. 1 and 2, as can be readily appreciated, any number of different architectures can be used without departing from the scope or spirit of the invention.

Figure 3:
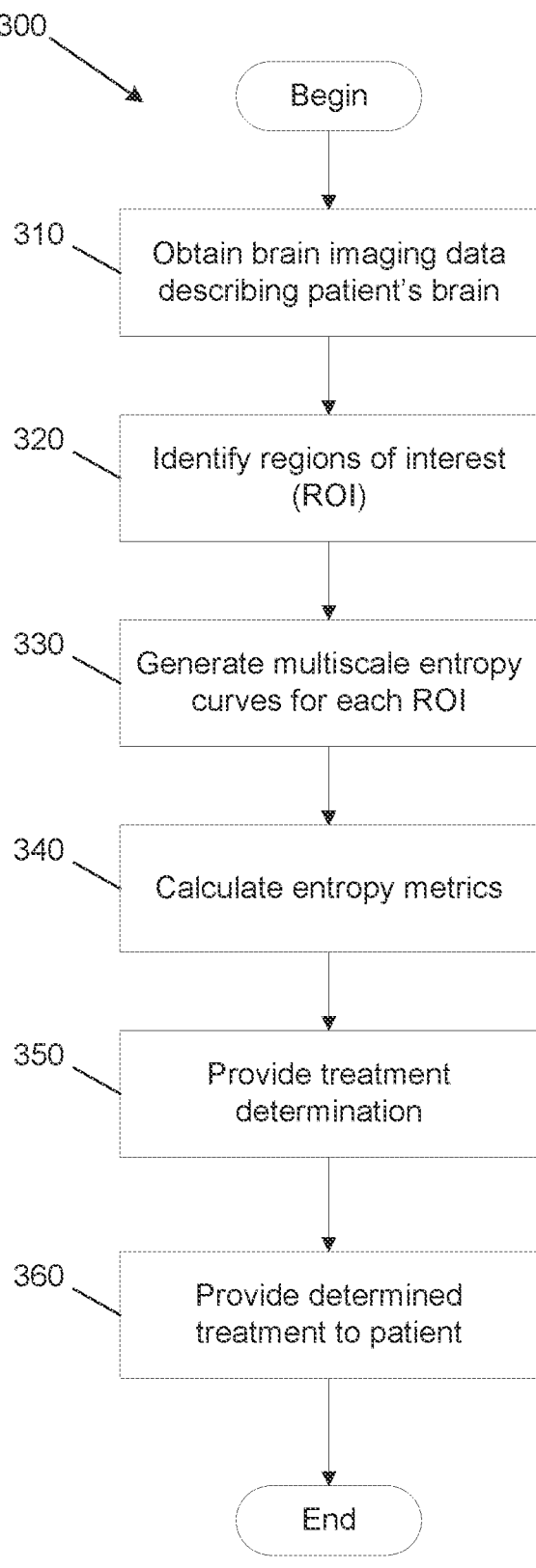
FIG. 3 is a flow chart for an entropy-based treatment method in accordance with an embodiment of the invention.

Turning now to FIG. 3, an entropy-based treatment process in accordance with an embodiment of the invention is illustrated. Process 300 includes obtaining (310) brain imaging data describing a patient's brain and identifying (320) regions of interest (ROI) within the brain imaging data. In many embodiments, regions of interest are determined using a parcellation method. In numerous embodiments, a standard parcellation method such as the Schaefer Atlas and/or any other atlas can be used. In various embodiments, the Schaefer Atlas with 100 parcellations is used, although others can be used as appropriate to the requirements of specific applications of embodiments of the invention.

Multiscale entropy curves for each ROI are generated (330) and used to calculate (340) entropy metrics. In many embodiments, sample entropy (often referred to as "SampEn") is calculated for each ROI. In various embodiments, multiscale sample entropy is calculated for each ROI. Additional entropy-based metrics can be derived from multiscale entropy curves, which are discussed further below. Based on the entropy metrics, a treatment can be selected (350) and subsequently provided (360). In many embodiments, the entropy metrics are used to classify a patient based on whether or not they are likely to significantly respond to a particular treatment. In numerous embodiments, the patient can be classified as a good candidate or a bad candidate for a neurostimulation protocol to treat depression. For example, in some embodiments, the patient is classified as either a good candidate or a bad candidate for treatment of depression using aTBS (now commercially referred to as Stanford Accelerated Intelligent Neuromodulation Therapy, "SAINT"). Additional information regarding aTBS can be found in U.S. Pat. No. 10,595,735 titled "Systems and Methods for Personalized Clinical Applications of Accelerated Theta-Burst Stimulation" granted Mar. 24, 2020, the disclosure of which is hereby incorporated by reference in its entirety. In many embodiments, if a patient is deemed to be a good candidate, they are provided with the respective treatment.

Classification of patients based on entropy metrics can be a complex process. In numerous embodiments, a machine learning model can be used to decipher brain imaging data in order to classify any arbitrary patient. In order to better focus the machine learning model and achieve more accurate results, in numerous embodiments entropy metrics are used to represent the brain imaging data which are in turn provided to the machine learning model which can be trained on a training data set of entropy metrics for given patients annotated with treatment outcomes. Turning now to FIG. 4, another entropy-based treatment process in accordance with an embodiment of the invention is illustrated.

Process 400 includes obtaining (405) an fMRI of a patient's brain. ROIs are identified (410) in the fMRI. The multiscale sample entropy equation is then parameterized based on the BOLD time-series for each ROI. Multiscale sample entropy can be parameterized using an embedded dimension value (m), a similarity metric (r), and a coarsegraining coefficient (r). In many embodiments, m=2, and r=0.5, however these values can be perturbed depending on goal and available compute as appropriate to the requirements of specific applications of embodiments of the invention, for example (but not limited to, m between 1 and 3, and r between 0.15 to 0.8. However, in numerous embodiments, τ is set such that the number of samples per time-scale are close to or greater than 50. τ that fits these parameters can be computed based on the BOLD time-series obtained. Multiscale entropy is then calculated (420) using the parameterized equation for each ROI to produce an entropy curve for each ROI.

The area under each entropy curve is calculated (425). The area under the entropy curve for each ROI is divided by the number of time-scales to calculate (430) a complexity index. A Z-value is then estimated (435) using the Z-transform for each ROI based on its respective complexity index. A positive or negative value is assigned (440) to each ROI based on the sign of the Z-value for the respective ROI, i.e. if Z-value >0, then assign ROI value +; if Z-value <0 then assign ROI value −. A similarity index is then calculated (445) by computing the pairwise distance between each pair of ROIs based on the entropy curves. In many embodiments, city block distance (also referred to as "Manhattan distance") is calculated, although other distance calculations can be applied without departing from the scope or spirit of the invention. In many embodiments, a large distance magnitude suggests a unique ROI compared to the other. However, the direction of the uniqueness is ambiguous as all the distance metrics are positive. The similarity index for each ROI is signed (450) using the ROI's assigned value.

The signed similarity indices are then provided to a machine learning model to classify (455) the patient. In many embodiments, the machine learning model is a supervised machine learning model trained on ground truth similarity indices annotated with treatment outcomes. In various embodiments, the machine learning model is a Naïve-Bayes model which tends to work well when there is a high-probability of patients responding well to the treatment at issue. However, other machine learning classification models can be used based on the type(s) of condition, type(s) of treatments, and/or any other parameter. For example, support vector machines, regressions, neural networks, and/or any other type of model can be used to classify patients as appropriate to the requirements of specific applications of embodiments of the invention. In various embodiments, if a patient is classified as a responder, then they are provided (460) the treatment.

Furthermore, in some embodiments, the raw value of the signed similarity index for the ROI corresponding to the subgenual anterior cingulate (sgACC) can be used for the specific identification of treatment viability in depression patients without the use of a machine learning model. That is, in various embodiments, if the signed similarity index is greater than +0.33, then treatment using aTBS is considered viable. In some embodiments, a positive signed similarity index is sufficient to determine that treatment using aTBS is viable.

Although specific systems and methods are discussed herein, many different methods and system architectures can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A method for treating a neurological condition, comprising:
    obtaining a functional magnetic resonance imaging (fMRI) scan of a patient's brain;
    identifying a plurality of regions of interest (ROIs) in the fMRI scan;
    calculating entropy metrics for each ROI in the plurality of regions of interest;
    selecting a treatment from a plurality of treatments for the neurological condition based on the entropy metrics; and
    provide the selected treatment to the patient.

2. The method for treating a neurological condition of claim 1, wherein the neurological condition is major depressive disorder, and the plurality of treatments comprise accelerated theta burst stimulation (aTBS) and pharmacological treatment.

3. The method for treating a neurological condition of claim 1, wherein calculating entropy metrics comprises:
    generating multiscale entropy curves for each ROI;
    calculating the area under each entropy curve;
    assigning each ROI as positive or negative sign based on the entropy curve of each ROI;
    generating a similarity index for each ROI; and
    signing the similarity index for each ROI using the assigned sign of each ROI.

4. The method for treating a neurological condition of claim 3, wherein selecting a treatment further comprises providing the signed similarity index to a machine learning model.

5. The method for treating a neurological condition of claim 4, wherein the machine learning model is trained using a training data set comprising signed similarity indices annotated with treatment outcomes.

6. The method for treating a neurological condition of claim 4, wherein the machine learning model is a Naïve-Bayes model.

7. The method for treating a neurological condition of claim 3, wherein generating multiscale entropy curves for each ROI comprises parameterizing a multiscale entropy equation such that τ is set such that a number of samples per time-scale is greater than 50.

8. The method for treating a neurological condition of claim 3, wherein assigning each ROI as positive or negative sign comprises performing a Z-transform.

9. The method for treating a neurological condition of claim 3, wherein generating a similarity index comprises calculating pairwise distance between each pair of ROIs based on the entropy curves.

10. The method for treating a neurological condition of claim 9, wherein pairwise distance is calculated using Manhattan distance.

11. A system for treating a neurological condition, comprising:
    a processor; and
    a memory, the memory containing a treatment prediction application that configures the processor to:
        obtain a functional magnetic resonance imaging (fMRI) scan of a patient's brain;
        identify a plurality of regions of interest (ROIs) in the fMRI scan;
        calculate entropy metrics for each ROI in the plurality of regions of interest;

select a treatment from a plurality of treatments for the neurological condition based on the entropy metrics; and provide the selected treatment as a recommended treatment for the patient.

12. The system for treating a neurological condition of claim 11, wherein the neurological condition is major depressive disorder, and the plurality of treatments comprise accelerated theta burst stimulation (aTBS) and pharmacological treatment.

13. The system for treating a neurological condition of claim 11, wherein to calculate entropy metrics, the treatment prediction application further directs the processor to:

generate multiscale entropy curves for each ROI;

calculate the area under each entropy curve;

assign each ROI as positive or negative sign based on the entropy curve of each ROI;

generate a similarity index for each ROI; and sign the similarity index for each ROI using the assigned sign of each ROI.

14. The system for treating a neurological condition of claim 13, wherein to select a treatment, the treatment prediction application further directs the processor to provide the signed similarity index to a machine learning model.

15. The system for treating a neurological condition of claim 14, wherein the machine learning model is trained using a training data set comprising signed similarity indices annotated with treatment outcomes.

16. The system for treating a neurological condition of claim 14, wherein the machine learning model is a Naïve-Bayes model.

17. The system for treating a neurological condition of claim 13, wherein to generate multiscale entropy curves for each ROI, the treatment prediction application further directs the processor to parameterize a multiscale entropy equation such that $\tau$ is set such that a number of samples per time-scale is greater than 50.

18. The system for treating a neurological condition of claim 13, wherein to assign each ROI as positive or negative sign, the treatment prediction application further directs the processor to perform a Z-transform.

19. The system for treating a neurological condition of claim 13, wherein to generate a similarity index, the treatment prediction application further directs the processor to calculate pairwise distance between each pair of ROIs based on the entropy curves.

20. The system for treating a neurological condition of claim 19, wherein pairwise distance is calculated using Manhattan distance.

* * * * *